(12) United States Patent
Zheng et al.

(10) Patent No.: US 7,399,603 B2
(45) Date of Patent: Jul. 15, 2008

(54) ANTIBODIES FOR DISCRIMINATION OF PRIONS

(75) Inventors: Jian Zheng, Raritan, NJ (US); Steve Stanley Alexander, Flemington, NJ (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 452 days.

(21) Appl. No.: 10/740,025

(22) Filed: Dec. 18, 2003

(65) Prior Publication Data
US 2004/0180367 A1    Sep. 16, 2004

Related U.S. Application Data

(60) Provisional application No. 60/446,217, filed on Feb. 10, 2003, provisional application No. 60/434,627, filed on Dec. 19, 2002.

(51) Int. Cl.
*G01N 33/68* (2006.01)

(52) U.S. Cl. ...................... 435/7.92; 435/69.3

(58) Field of Classification Search ........................ None
See application file for complete search history.

(56) References Cited

U.S. PATENT DOCUMENTS 4,806,627 A    2/1989 Kascsak et al.
5,011,770 A *  4/1991 Kung et al. ................... 435/6
6,426,409 B1 * 7/2002 Winnacker et al. ......... 536/23.1
6,528,269 B1 * 3/2003 Sy et al. ...................... 435/7.1

FOREIGN PATENT DOCUMENTS

EP    0 861 900    9/1998
WO    WO 97/32602  9/1997

OTHER PUBLICATIONS

Cordeiro Yralma et al., "DNA Converts Cellular Prion Protein into the Beta-Sheet Conformation and Inhibits Prion Peptide Aggregation", Journal of Biological Chemistry, vol. 276, No. 52, pp. 49400-49409, Dec. 2001.
Cunnington P. G., et al., "Absence fo Antibodies to Double Stranded RNA and DNA in Sera of Scrapie Infected Sheep and Mice" International Research Communications System Medical Science, vol. 4, No. 6, 1976, p. 250, (1976).
Partial European Search Report, dated May 14, 1004, for European Appln. No. EP 04 25 0678.

* cited by examiner

*Primary Examiner*—Bruce Campell
*Assistant Examiner*—Agnieszka Boesen
(74) *Attorney, Agent, or Firm*—Susan J. Timian

(57) ABSTRACT

In the present invention, we described the use of anti-DNA antibody for the detection of prions and diagnosis of Transmissible Spongiform Encephalopathies (TSE) diseases in animals and humans.

6 Claims, 10 Drawing Sheets

ANTIBODIES FOR DISCRIMINATION OF PRIONS

CROSS REFERENCE TO RELATED APPLICATIONS

Figure 1:
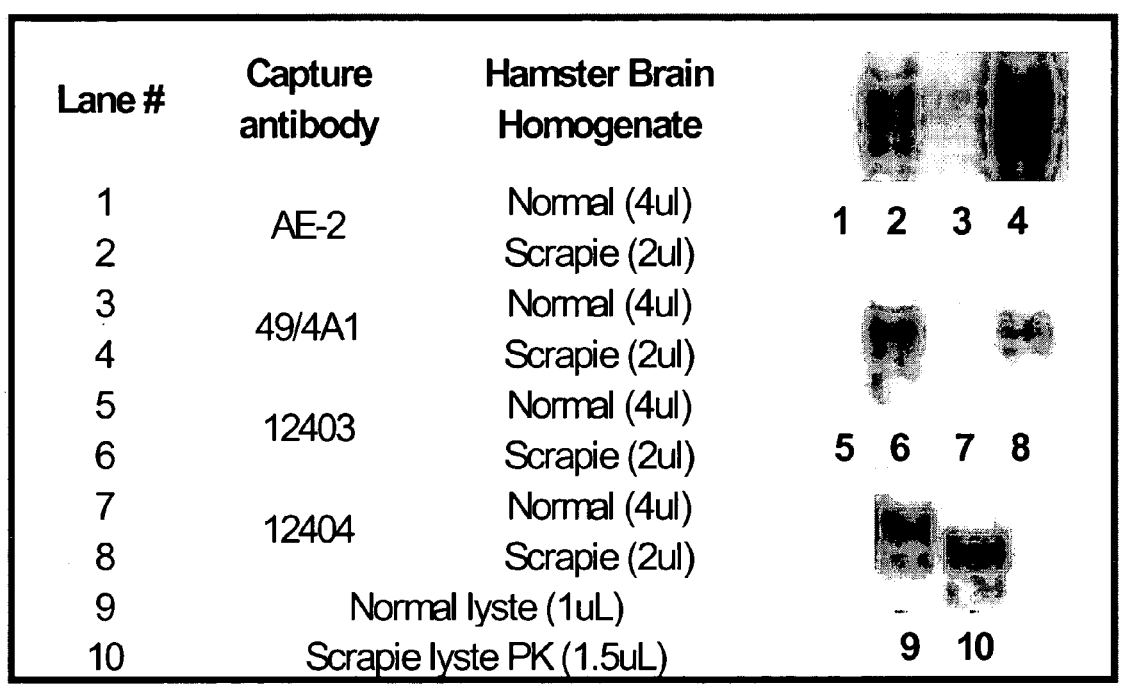
Figure 2:
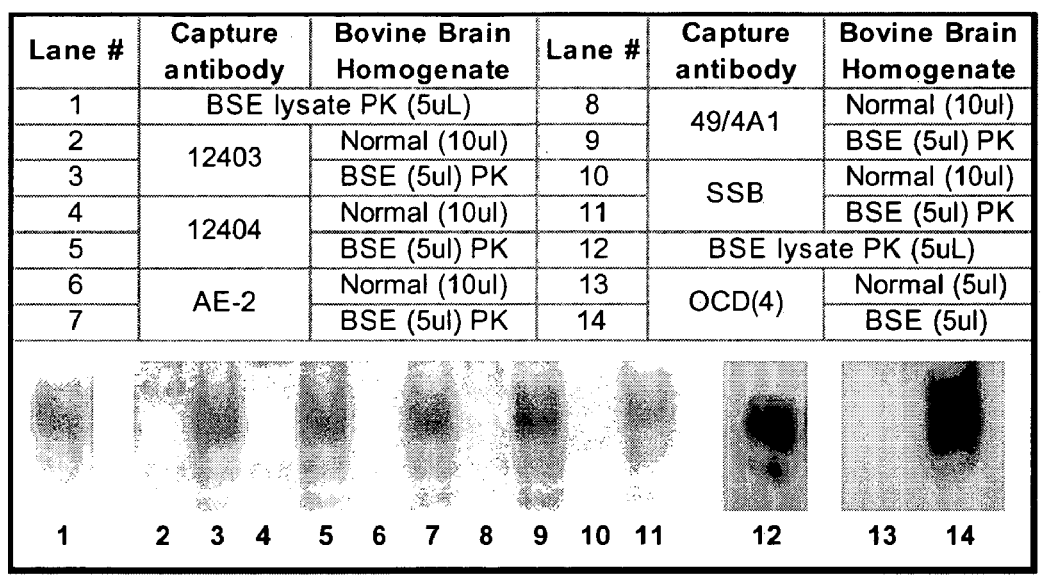
Figure 3:
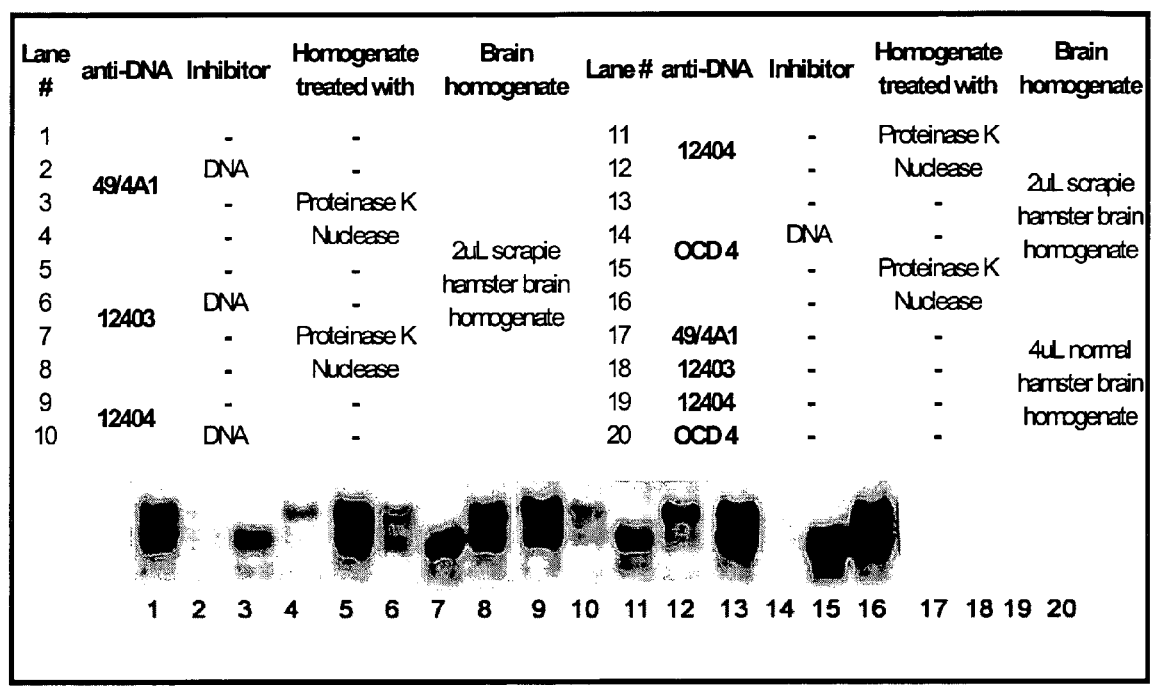

This application claims the benefit of U.S. Provisional Application No. 60/434,627, filed Dec. 19, 2002 and U.S. Provisional Application No. 60/446,217, filed Feb. 10, 2003.

FIELD OF THE INVENTION

In the present invention, we described the use of anti-DNA antibody (also referred to hereinafter as "an anti-nucleic acid antibody") for the detection of prions and diagnosis of Transmissible Spongiform Encephalopathies (TSE) diseases in animals and humans.

BACKGROUND OF THE INVENTION

Transmissible spongiform encephalopathies (TSEs) comprise a group of rapidly progressing, neurodegenerative fatal diseases that affect both humans and animals. TSEs have clinical and neuropathological characteristics which include devastating dementia, pyramidal and extrapyramidal signs with myoclonus, multifocal spongiform changes, astrogliosis, amyloid plaques, neuronal loss, absence of inflammatory reaction and are usually characterized by a long incubation period.

In animals, a commonly known example of TSE disease recognized for over 200 years, is scrapie, which is found in sheep and goats (McGowan 1922). Other animal TSE diseases have also been described, such as transmissible mink encephalopathy (TME, Marsh 1976), chronic wasting disease of mule deer and elk (CWD, Williams 1980), bovine spongiform encephalopathy (BSE, commonly known as "mad-cow" disease (Wells 1987), and the more recently described feline spongiform encephalopathy of domestic cats, pumas, and cheetahs (Wyatt 1991).

In humans, TSEs have been traditionally classified into Creutzfeldt-Jakob disease (CJD), kuru, Gerstmann-Sträussler-Scheinker syndrome (GSS) and fatal familial insomnia (FFI). Among them, Kuru has been described only in the Fore linguistic group of New Guinea. For many years after its first recognition in 1957, kuru was the most common cause of death among women in the affected population, but its occurrence has declined because of the cessation of cannibalism that had facilitated disease transmission. As of today, only a few cases still occur due to the long incubation periods typical of this condition.

Although these rare neurodegenerative disorders occur in about 0.5 to one person per million worldwide (Brown 1987), TSEs attracted considerable public attention because of the unique biology and concerns about a onset of the epidemic of a newly recognized bovine spongiform encephalopathy (BSE) and its potential effects on human. There is mounting evidence that through dietary exposure to BSE infected tissues, it has poses a serious threat to public health and has resulted in an increased number of incidents of a newly recognized variant form of CJD (vCJD). Until now, there have been more than 100 cases of vCJD reported, a majority which are located in UK.

It is believed that prions are the pathogenic agent causing TSE. Many efforts have been directed towards identifying the etiological agent that causes TSEs. Early on, the transmissibility of TSE disease had been experimentally demonstrated in many cases, kuru and CJD from humans to chimpanzees (Gajdusek 1966, Gibbs 1968), transmissible scrapie from sheep to sheep (Cuillé 1936) and across species to goat (Pattison 1957). The most significant breakthrough was the successful transmission of scrapie to mice, by Richard Chandler in 1961 (Chandler 1961). Chandler's discovery greatly facilitated TSE research by providing an experimental model that was cheaper and easier to manipulate. Although all of the above modes of transmission were demonstrated experimentally, the cause of recent BSE in cattle and new variant CJD in human (vCJD) was considered a consequence of dietary exposure to the mix of scrapie sheep carcasses rendered for animal feed in the case of BSE (Brown 1997), and to beef from cattle affected with BSE in the case of vCJD (Bruce 1997).

It was suggested that TSE diseases might be caused by "slow viruses" or viroids (Gajdusek 1977). However, the extreme resistance of scrapie infectivity to radiation, nucleases, and other reagents damaging to genetic materials are inconsistent with the "virus" theory. Moreover, the infectious TSE agent could tolerate very high levels of heat and high concentrations of formaldehyde (Pattison 1965) while still able to replicate with the 'incubation period' varying from a few months to over a year (Alper 1966).

All these "unusual" characteristics of the TSE infectious agent led Dr. Stanley Prusiner to propose the concept of "prions" in 1982 (Prusiner 1982). Prion (PrP), which stands for nucleic acid-free proteinaceous infectious particle, is a glycoprotein present in humans and animals. In humans, it is encoded by PRNP on chromosome 20 (Robakis 1986). The cellular form of this protein ($PrP^C$) has two N-link glycosylation sites and a GPI anchor at the C-terminus. It has been most commonly found in neurons, and, to a much lower extent, it has also been found in other cells such as leucocytes, monocytes and platelets (Holada 2000). Furthermore, a soluble form of PrP that lacks the glycolipid anchor was detected in murine and human serum. The transmissible scrapie disease form of the prion protein ($PrP^{Sc}$) is a protease resistant isoform of its cellular precursor and is predominantly found in brain. At much lower level, it has also been found in tonsil, spleen, and lymph nodes in vCJD patients (Parizek 2001). The conversion from $PrP^C$ to $PrP^{Sc}$ is believed to be accomplished through a conformational change within the protein. Although there is still ambiguity concerning the mechanism of the conversion, much experimental evidence indicates that in the presence of $PrP^{Sc}$, normal $PrP^C$, acting as a substrate, undergoes a conformational structure change, and becomes $PrP^{Sc}$. This process of propagation involves replicating the conformation of $PrP^{Sc}$ in $PrP^C$ and results in $PrP^{Sc}$ aggregation and amyloid rod formation, hence causing cell death (Hope 1986, Horwich 1997). As a result of Prusiner's concept of the "prion" as an infectious agent responsible for scrapie disease, and by extension, that of all TSE diseases gave rise to the notion of what are commonly referred to as Prion diseases to describe a class of pathologies believed to be linked to this protein.

Characteristics of $PrP^C$ and $PrP^{Sc}$

The major property that differentiates $PrP^C$ and $PrP^{Sc}$ is their distinct conformation. The structural change from $PrP^C$ to $PrP^{Sc}$ is most supported by a crucial conformational change, involving a substantial increase in the amount of beta-sheet structure of the protein, with possibly a small decrease in the amount of alpha-helix, indicated by circular dichroism and infrared spectroscopy (Pan 1993, Caughey 1991). The solution structure of a fragment of the mouse $PrP^C$ has allowed a direct determination of secondary structure content of a portion of $PrP^C$ (121-231) by NMR (Riek 1996).

Protease resistance is another characteristic that distinguishes PrP$^{Sc}$ from PrP$^C$. In cultured cells and brain or in samples from many patients with GSS, PrP$^{Sc}$ is smaller than its cellular prion precursor PrP$^C$. Even though cellular prion and scrapie prion are two isoform of same PRNP genomic product, PrP$^C$ is completely degraded by Proteinase K treatment while PrP$^{Sc}$ undergoes only limited digestion. The digestion yields a form of protein referred to as PrP 27-30 in which the N-terminus has been removed. PrP 27-30 has been postulated to be the PrP$^{Sc}$ core required for PrP$^C$ hosted PrP$^{Sc}$ replication. The protease treated prion molecule, PrP 27-30 or PrP$^{res}$, is tightly linked to scrapie infectivity (Gabizon 1988), and provides additional evidence that PrP$^{Sc}$ is an infectious protein.

An additional attribute, perhaps linked to the significant increase in β-sheet structure and concomitant protease-resistance, is the observed difference in solubility between PrP$^{Sc}$ and PrP$^C$. While PrP$^C$ is a soluble protein, the PrP$^{Sc}$ isoform is highly insoluble. Furthermore, PrP$^C$ is found attached to the surface of neurons through a GPI tail anchored into membrane (Shyng 1994) while PrP$^{res}$ is found in the cytoplasm of affected cells (Taraboulos 1990), most likely associated with late endosomal and lysosomal compartments (Arnold 1995), and PrP$^{Sc}$ is also localized in amorphous aggregates in enriched fractions from infected brain (Meyer 1986). Interestingly, a disease-associated mutant PrP, the PrP$^{159stop}$ mutant was found exclusively in nucleus (Lorenz 2002).

There is mounting evidence indicating a tight linkage between scrapie infectivity and PrP 27-30. Even in the purest samples, the estimated ratio of PrP molecules to infectious units is ~$10^4$ to $10^5$ (Horwich 1997, Bolton 2001). At such low levels of infectivity, it is possible that other components, co-factors, or covalent modifications, are required for infectivity. The transgenic studies on the susceptibility of mice expressing chimeric human-mouse PrP$^C$ suggest the presence of at least one host factor other than PrP$^C$, tentatively termed factor X, which might function as a molecular chaperone in the formation of PrP$^{Sc}$ (Telling 1995).

Other Molecules Associated with Prion Pathogen

About 15 to 20 strains of scrapie have been identified based on their incubation period and lesion patterns in the inbred mice. After a serially inoculation passage in inbred mice homozygous for a single PRNP genotype, all the scrapie strains retained their original disease profile. These observations led investigators to question whether varied phenotypic strains were dominated by different conformation isoforms of same cellular prion precursor, a possibility suggested by conformation-dependent immunoassay (Safar 1998), or whether these strains were a result of various PrP$^{Sc}$ associated molecules.

Many researchers have identified various nonprotein molecules that are bound to prion proteins. The precise biological and physiological roles remain the topic of further investigation. Copper and zinc have been demonstrated to bind to PrP$^C$. In vitro, these divalent metals may contribute to prion superoxide dismutase (SOD)-like activity. Such SOD-like activity and copper content are dramatically reduced in scrapie-infected brain (Wong 2001).

In addition, prion rods, composed mainly of insoluble aggregates of the N-terminally truncated prion protein (PrP 27-30) are found to be associated with 1,4-linked glucose units. Sphingolipids, polysaccharide and other membrane components were also found in prion aggregates (Appel 1999, Klein 1998). The interaction between prion protein and lipid membranes could play a role in PrP conversion. For example, the negatively charged lipid membrane-inserted conformation of PrP is richer in β-sheet structure while the binding of PrP to raft-like membranes induces the formation of α-helical structure (Sanghera 2002).

In early 1990's, Snow et al, studying Gerstmann-Sträussler-Scheinker syndrome, Creutzfeldt-Jakob disease and scrapie, have documented the association of sulfated proteoglygan to the prion protein amyloid plaques (Snow 1990). In an immunohistochemistry study using heparan sulfate antibodies (anti-HS) and heparan sulfate proteoglycan antibodies (anti-HSPG), McBride has demonstrated the correlation and association between HSPG and abnormal PrP in scrapie-infected mice brain. This correlation and association was observed as early as 70 days post-infection and throughout the course of the disease (McBride 1998). In in vitro conversion from PrP$^C$ to PrP$^{Sc}$ and in prion infectivity reconstitution experiments, sulfate glycans have been shown either to facilitate the conversion or to escalate infectivity (Wong 2001, Shaked 2001a). With recombinant GST::full-length prion and GST::prion fragment, Warner recently demonstrated direct binding of recombinant prion to heparin and heparan sulfate (Warner 2002). The peptide region 23-52 in prion sequence was positive in all HS and HSPG binding tests. Since the peptide failed to compete with full-length prion for binding to heparin, the author suggested that there might be another major GAG-binding site in intact PrP$^C$. Another noteworthy observation is that GAGs from different species (bovine and porcine) or from different organs (lung, kidney and intestine) have shown different affinities for prion binding. The difference in affinity may be due to prion sequence itself, or may depend on the presence of particular sugar unit in the tested GAGs.

Through a mechanism that is perhaps different from that by which glycans participate in the conversion of PrP$^C$ to PrP$^{Sc}$, DNA could also convert cellular prion protein into β-sheet conformation (Cordeiro 2001). Nandi demonstrated that prion peptide 106-126 is the region that participated in the nucleic acid-prion complex association (Nandi 1998). Interestingly, not only was PK resistant amyloid aggregate obtained from the interaction between prion protein and nucleic acids, the nucleic acid morphology also changed to condensed globular structures, similar to nucleic acid structures induced by the HIV-1 NCp7 protein, but not to the structure induced by histones (Nandi 2001). Based on those in vitro conformation and conversion studies, it was hypothesized that DNA would act as a guardian of the PrP$^{Sc}$ conformation as well as a catalyst to facilitate PrP$^{Sc}$ conversion and aggregation (Cordeiro 2001).

Whether one accepts or rejects the "protein only" or "prion only" hypothesis, the effort to link inherited information to TSE disease or the search for genetic make up related to TSE disease has never stopped. The presence of a tightly bound RNA or DNA molecule in the prion particle was proposed to explain propagation of different strains of scrapie agent with distinct phenotypes in animals homozygous for the PRNP gene (Weissmann 1991). Analysis of highly purified scrapie prions by return refocusing gel electrophoresis revealed the small size of remaining nucleic acids, although the size of extracted nucleotides was too small to encode any meaningful protein (Kellings 1992). In a recent report, however, Narang indicated that animals inoculated with ssDNA purified from scrapie-hamster brains mixed with non-pathogenic prion developed clinical disease (Narang 2002). Based on his findings, he postulated that the "accessory protein" coded by the ssDNA may be involved in PrP$^C$ to PrP$^{Sc}$ conversion. Although the role of nucleic acids in prion-associated disease is controversial, it is clear that PrP$^{Sc}$ aggregates are tightly associated with these small molecules.

Infectivity and Transmissibility of Prion Diseases

Classic CJD in human has been grouped into three etiological types: sporadic (CJD), inherited (GSS or FFI), and acquired, which is very rare and includes diseases such as kuru and iatrogenic CJD. There is no hard evidence indicating any of CJD diseases is related to animal TSEs that may have crossed species barriers. The epidemic of kuru has provided the largest body of evidence of acquired human prion disease. Searching for risk factors and possible sources of infection in sporadic CJD patients revealed no significant correlation of disease to diet, blood transfusion or receiving other blood product. However, after intracerebral inoculation to mice, the infectivity in blood obtained from CJD patients indicated the possible presence of the CJD agent (Manuelidis 1985, Tateishi 1985).

BSE appears to have originated from dietary exposure. Nutritional supplements of processed meat and bone meal derived from scrapie disease infected carcasses were used to feed cattle livestock and other captive animals. In spite of BSE originating from scrapie, no case of de novo infection or cow-to-cow transmission has been reported.

There is mounting evidence, however, that links vCJD to BSE, The growing epidemiological data locates the majority of vCJD cases in UK where the overwhelming majority of BSE cases have also been reported. The link between vCJD and BSE is further supported by the neuropathologic evidence obtained from BSE-adapted macaques, the nearest model to humans (Bruce 1997), and from the study on inbred mice inoculated with the agent causing BSE and vCJD (Lasmézas 1996).

Although no vCJD patient has been documented as a victim of human-to-human transmission, the close link between BSE and vCJD attracted considerable attention. Concerns about human infection have been based on the observation that $PrP^{Sc}$ is readily detectable in BSE and vCJD lymphoreticular tissues but not in classic CJD (Hill 1997), followed by the presumption that scrapie pathogen from sheep passage to cattle may have altered host range and become more adaptable to human. Experimental precedents for such behavior are well known: passage of mouse-adapted strains of scrapie through hamsters altered their transmissibility on back passage to mice (Kimberlin 1987, Kimberlin 1989); human strains of kuru or CJD did not transmit to ferrets or goats until passaged through primates or cats (Gibbs 1979); and a bovine strain of BSE did not transmit to hamsters until passaged through mice (Foster 1994). Alternatively, if BSE originated from a spontaneous mutation in cattle, experimental studies of species susceptibility to this new strain of transmissible spongiform encephalopathy (TSE) had not sufficiently advanced to predict that humans would not be susceptible.

In addition to CJD infectivity in blood described above, other TSE infectivity in blood has also been demonstrated in various experimental animals. Most blood for infectivity studies was obtained from TSE-adapted rodents such as mice and hamsters. The only exception was a study conducted in the sheep model. In this experiment, a sheep transfused with whole blood, taken from another sheep inoculated with BSE brain lysate, developed symptoms of BSE (Houston 2000, Hunter 2002). However, these experimental results yet need to be fully evaluated. The infectivity in blood has been established in rodent animals through intracerebral and intravenous transmission with mice-adapted BSE, mice-adapted vCJD and other rodent animal adapted TSE strains. Although the infectivity in lymphocyte-rich buffy-coat is greater than in plasma, it only accounts for relatively a small portion when compared to whole blood inoculums. The molecular definition of this infectious agent present in the blood is still under investigation. It is anticipated that finding of such infectious agent in blood would help us to better understand the relationship between $PrP^{Sc}$ and TSE disease.

Study on human CJD and vCJD disease indicated that genomic susceptibility may yet be another factor that may influence the spread of TSE in humans. The majority of sporadic CJD patients were found to be homozygous for Met/Met or for Val/Val at codon 129 (Belay 1999). Nevertheless, all reported vCJD cases have been found to be homozygous for Met/Met.

The size and duration of vCJD epidemic still remains uncertain. Depending on the assumptions made and the modeling calculations employed, different predictions were proposed. One estimation of total vJCD predicts as few as 205 cases (Valleron 2001). On the other hand, another prediction for vCJD mortality for the next 80 years ranges from 50 to 50,000 if infection comes only from BSE. It could reach up to 150,000 if BSE is proven to infect sheep and if subsequently it is allowed to enter human food chain (Ferguson 2002). Although it is impossible to make accurate predictions if the necessary parameters are either mistaken or not available, one thing is certain that if vCJD infectivity is present in blood, any prediction will be an underestimate. In addition, vCJD has been proven to be a new disease entity and not simply the result of increased surveillance of CJD in humans (Hillier 2002).

Countermeasures have been taken by government to eliminate the spread of BSE incidence. Ruminant protein feed was banned in US and UK (1988). A series of measures have also been taken to prevent potentially infected meat from entering human food chain. To further reduce the human risk, FDA and CBER has issued a new policy in Aug. 2001, which indefinitely defers any human blood donor who stayed cumulative $\geq 6$ month during 1980-1996 in the United Kingdom (FDA 2001).

Diagnostic Assay for Prion Disease

Clinical symptoms of prion disease often overlap with those of other neuronal degenerative diseases that make diagnosis difficult. So far, PK resistant PrP 27-30 is the only protein marker linked to TSE disease. Therefore, the detection of this agent has become the focus of assay development. However the development of monoclonal antibody specific for $PrP^{Sc}$ was extremely difficult, not only because pathogenic $PrP^{Sc}$ isoform and normal cellular $PrP^{C}$ are two conformers of the same protein with an identical primary sequence, but also because the prion appears to be a weak immunogen. The only antibody reported to be able to recognize $PrP^{Sc}$ specifically is not practically useful (Korth 1997). Other prion sequence-specific monoclonal and polyclonal antibodies are unable to distinguish $PrP^{Sc}$ from $PrP^{C}$. Nevertheless, these antibodies (such as 3F4, 6H4 described in U.S. Pat. No. 4,806,627 and EP0861900.) are still commonly in use for capture or for detection of prion protein in combination with sample treatment and separation techniques to isolate $PrP^{Sc}$ from $PrP^{C}$ (Korth 1997, Kascsak 1987).

Since the outbreak of BSE in 1986, all commercially available tests for prion disease use, as their sample source, tissues taken from postmortem animals and humans. Among those, a tissue homogenate-based $PrP^{Sc}$ assay, referred to as DELFIA (dissociation-enhanced lanthanide fluoroimmunoassay), was developed for the detection of scrapie prion (Barnard 2000 and a method described in US20020137114A1). It requires a protein denaturation step using GdnHCl, in combination with optional sample PK treatment and $PrP^{Sc}$ enrichment by sodium phosphotungstic acid (NaPTA) precipitation. Since the transformation of $PrP^{C}$ to $PrP^{Sc}$ is accompanied by the burial of epitopes near the N terminus of PrP, in DELFIA, monoclonal antibodies directed against the N-terminus of PrP are used to measure the difference of mAb binding affinity to the α-helical and β-sheet conformations before and after PrP denaturation (Peretz 1997). Another conformational-dependent immunoassay (CDI) combined with ELISA and fluorescence detection (Safar 1998, US 20010001061A1, US20020001817A1) was described in conformation studies in PrP$^{Sc}$ strains.

In a tissue distribution study of PrP$^{Sc}$ in vCJD patients, an improved NaPTA precipitation was described to enrich PrP$^{Sc}$ from brain and from other peripheral tissue homogenates (Wadsworth 2001). The modification employed endonuclease treatment to reduce sample viscosity prior to NaPTA precipitation. The recovery of PrP$^{Sc}$ in the precipitated pellet was reported to be consistently greater than 90% while recovery of PrP$^C$ was about 5%. After PK digestion, the presence of PK resistant prion was verified in Western blot using 3F4 monoclonal antibody.

In another similar immunoblot assay, PK digestion was also used to eliminate PrP$^C$. 6H4 was then used to determine the presence of PrP$^{Sc}$ (Schaller 1999). Based on this first generation assay, a second-generation luminescence immunoassay was developed in which 6H4 was coated on plates as a capture antibody. The horseradish peroxidase (POD)-conjugated detection antibody used was a mouse monoclonal anti-PrP antibody, able to form a complex with PrP27-30 bound to 6H4 (Biffiger 2002).

The European Commission in 1999 evaluated 4 BSE test kits from different manufacturers (Moynagh 1999). They all used bovine brain tissue as a sample source, and all required a separate sample preparation procedure. Depending on the kit instructions, the brain tissue homogenate needed to be processed, including denaturation, PK digestion or PrP$^{Sc}$ enrichment. The assay detection systems employed in DELFA, immunoblot, or in plate ELISA formats used either chemiluminescent or a colorimetric substrate.

In order to control the spread of the disease in the absence of a live-animal screening test, an extensive slaughter of cattle was carried out once an affected animal was identified within a herd. The urgency for a live animal diagnosis assay was reinforced when the first cases of variant Creutzfeldt-Jakob disease was reported in 1996.

Antemortem TSE diagnosis development presents three major difficulties: (1) insufficient sensitivity—Except in brain tissue, PrP$^{Sc}$ concentrations in other tissues or fluids is considered to be very low. Therefore, a highly sensitive technique is required for detection. (2) Appropriate sample treatment—Any protein denaturation or PK digestion process may have a potential impact on pathogenic PrP$^{Sc}$ structure, with the possibility of causing a false negative result. For example, it has been suggested that an intermediate form of PrP$^{Sc}$ may not be PK resistant (Horiuchi 1999, Jackson1999, Swietnicki 2000). And (3), the lack of PrP$^{Sc}$-specific antibodies and the incompletely characterized molecular relationship between the pathogenic agent and PrP$^{Sc}$ in blood make it difficult to design an assay format for antemortem diagnosis.

A possible approach to boost the sensitivity is in-vitro amplification of PrP$^{Sc}$. It has been reported that when PrP$^{Sc}$ was present, repetitive cycles of sonication could induce protease-sensitive cellular PrP to form protease resistant aggregates. The authors explained that in this "protein-misfolding cyclic amplification" (PMCA) process, sonication could disrupt newly formed aggregates and generate multiple smaller units for the continued formation of new PrP$^{Sc}$ (Saborio 2001, WO0204954). At the end of 40 PMCA cycles, the sample was subjected to PK digestion and detected by immunoblot. It claimed that the amplification generated more than 30-fold protease resistant PrP. Since proteinase resistant PrP were generated at the expense of the normal prion protein as substrate through amplification cycles, a large quantity of same-species normal prion was required. It has not been demonstrated whether normal prion from another species could also work as substrate, or prion protein from a recombinant source or from sources other than brain tissue could be used. Such evidence would be useful when detection of vCJD is desired.

Immunohistochemistry of third eyelid lymphoid tissue has been described for preclinical diagnosis of ovine scrapie (O'Rourke 2000, U.S. Pat. No. 6,165,784, U.S. Pat. No. 6,261,790). Relying on a small surgical procedure, the assay makes use of sheep peripheral tissue, the third eyelid lymphoid for scrapie detection. The immunohistochemistry used a cocktail of pan-specific monoclonal antibodies to differentiate one isoform from the other. Following formalin fixation to reduce PrP$^C$ reactivity, the sample is subjected to formic acid and heat pretreatments which enhance the PrP$^{Sc}$ reactivity. In spite of the fact that the assay is still tissue based and the observation that PrP$^{Sc}$ displayed poor immunoreactivity in immunohistochemistry staining unless treated with denaturing agents, this antemortem preclinical diagnosis has made a step towards live-animal test as well as provided a way of identification of scrapie-affected sheep during the early, preclinical stage of scrapie.

In addition to the traditional identification of pathogenic prion by eliminating cellular prion followed by non-discriminatory anti-prion antibody recognition, other reagents were found to be able to differentiate PrP$^{Sc}$ from PrP$^C$, such as plasminogen and fibrinogen. The mechanism of interaction between these human blood component proteins and PrP$^{Sc}$ is not clear. However, when immobilized on magnetic beads, plasminogen selectively precipitated PrP$^{Sc}$ from brain homogenates of mouse, human, cattle and sheep. The evidence provided suggested that a property common to PrP$^{Sc}$ of various species, rather than prion primary sequence or the specific tertiary structure of individual PrP$^{Sc}$ molecules, could be responsible for binding to plasminogen (Fischer 2000, Maissen 2001). The application for the use of plasminogen and other serum/plasma proteins for the capture and detection of pathogenic prion protein has been described in WO0200713 and in US20010053533A1 (Aguzzi 2001).

Recent investigations have identified a new isoform of the prion protein in the urine of animals and humans with prion disease (Shaked 2001b, WO0233420A2). This isoform, referred to as UPrP$^{Sc}$ by the investigators, was precipitable, PK resistant, and detectable only in infected individuals but not in normal controls. Most importantly, as indicated in their publication, UPrP$^{Sc}$ appeared long before the clinical signs developed in inoculated hamsters. However, when UPrP$^{Sc}$ isolated from scrapie hamster urine was inoculated back in normal hamster intracerebrally, it did not cause disease even after 270 days, well beyond the incubation period in which animal would develop clinical signs if comparable amount of brain derived PrP$^{Sc}$ had been inoculated. It is not impossible that those hamsters, inoculated intracerebrally with UPrP$^{Sc}$, were still in a subclinical or carrier state. Moreover, PK-resistant PrP was not found in the kidneys, which implies that this UPrP$^{Sc}$ could have originated from other organs and been transported to the urine via the blood. This important observation will undoubtedly lead to a better understanding of PrP metabolism.

Therefore there remains an unmet need for a better way to detect PrP$^{Sc}$ and diagnose TSE in humans and animals. The aim of the present invention is to provide a non-intrusive way to isolate, concentrate and monitor the TSE disease-related pathogenic prion protein. The invention, including the use of selective anti-DNA antibody to bind the PrP$^{Sc}$ through recognition of an associated binding partner, involves the discriminatory capture of PrP$^{Sc}$ but not cellular prion protein. We provide evidence of a high affinity association of nucleic acid to PrP$^{Sc}$, and we demonstrate that such nucleic acids::PrP$^{Sc}$ complex survived even after PK digestion and nuclease treatment.

SUMMARY OF THE INVENTION

The evidence provided in support of this invention demonstrated that PrP$^{Sc}$ is associated with high affinity to nucleic acid, mainly DNA as investigated. A similar association with nucleic acid was not observed with normal cellular PrP$^C$. The evidence also demonstrated that the association was strong, resistant to PK digestion and nuclease treatment, and that PrP$^{Sc}$ could be readily isolated by selective anti-DNA antibodies.

This invention relates to the use of anti-DNA antibodies to capture PrP$^{Sc}$ through nucleic acids associated with high affinity to PrP$^{Sc}$, in combination with any prion sequence-specific antibody for the detection of PrP$^{Sc}$.

In another aspect, this invention relates to the selective anti-DNA antibody, as described above, that preferably binds to pathogenic prion protein but not to the normal cellular form of prion protein.

In another aspect, this invention relates to the selective anti-DNA antibody, as described above, for the detection of PrP$^{Sc}$ through high affinity recognition of associated nucleic acids in combination of prion sequence specific antibodies.

In another aspect, this invention relates to the selective anti-DNA antibody, as described above, for the isolation, purification, capture, elimination and monitoring PrP$^{Sc}$ in biological reagent production.

In another aspect, this invention relates to compositions and kits for determining the presence of PrP$^{Sc}$, comprising anti-DNA antibody, as described above, for either capture or for detection step in the assay procedure.

In another aspect, this invention relates to compositions and kits for determining the presence of PrP$^{Sc}$ antibody produced in response to high affinity associated DNA as a binding partner to pathogenic prion protein.

In yet another aspect, this invention relates to anti-PrP$^{Sc}$ antibodies and their production using the said nucleic acids that can interact with and/or associate to $PrP^{sc}$, and their use in detecting nucleic acid::$PrP^{Sc}$ complex and prion disease infection.

In another aspect, this invention relates to a non-harsh sample treatment procedure involving nuclease digestion for the benefit of the use of selective anti-DNA antibody as described above.

Some examples of specific embodiments of the invention are as follows:

A method for discriminating between infectious and non-infectious prions comprising:
- first contacting a sample with an anti-nucleic acid antibody,
- then adding a prion specific antibody to form a complex between the anti-nucleic acid antibody, prion and prion specific antibody, and
- detecting the complexes.

A method for diagnosing transmissible spongiform encephalopathies in a patient comprising:
- drawing a sample from a patient,
- contacting a sample with an anti-nucleic acid antibody,
- then adding a prion specific antibody to form a complex between the anti-nucleic acid antibody, prion and prion specific antibody, and
- detecting the complexes, whereby detecting the complexes provides and indication of transmissible spongiform encephalopathies in a patient.

An immunoassay for detecting infectious prions comprising:
- providing a solid support having bound thereto an anti-nucleic acid antibody,
- contacting the solid support with a sample,
- washing the support to remove any unbound sample,
- contacting the solid support with a prion specific antibody, and
- carrying out a detection step to determine if prions are bound to the solid support.

A kit for the detection of infectious prions comprising
- a solid support having bound thereto an anti-nucleic acid antibody, and
- a labeled prion specific antibody.

An immunoassay for detecting infectious prions comprising:
- providing a solid support coated with an agent to bind an anti-nucleic acid antibody contacting the solid support with a sample,
- washing the support to remove any unbound sample,
- contacting the solid support with a prion specific antibody, and
- carrying out a detection step to determine if prions are bound to the solid support.

Another embodiment of the immunoassay described above provides a solid support coated or carrying an agent that is capable of binding the anti-nucleic acid antibody. For example, using avidin or streptavidin on the solid support and biotinylating the anti-nucleic acid antibody so that it binds to the solid support via the avidin or streptavidin.

A further embodiment of the invention is directed to a vaccine composition comprising anti-nucleic acid antibodies and a pharmaceutically acceptable carrier.

A method of treating a prion disease in a patient comprising administering a therapeutically effective amount of a vaccine composition comprising anti-nucleic acid antibodies and a pharmaceutically acceptable carrier.

A method of inducing neutralized infectious prions in a patient susceptible to or suffering from a prion disease comprising administering a therapeutically effective amount of a vaccine composition comprising anti-nucleic acid antibodies and a pharmaceutically acceptable carrier.

BRIEF DESCRIPTION OF THE DRAWINGS

FIG. 1: anti-DNA IP capture and immunoblot of scrapie hamster $PrP^{Sc}$. Hamster scrapie $PrP^{Sc}$ was immunocaptured by anti-DNA antibodies followed by SDS-PAGE and 3F4 immunoblot. Results were obtained from three separate experiments (Lane# 1-4, 5-8 and 9-10).

FIG. 2: IP capture and immunoblot of BSE PrPSc. BSE $PrP^{Sc}$ was detected by anti-DNA antibodies and DNA binding protein through immunoprecipitation (IP) followed by 6H4 immunoblot. Results were obtained from two separate experiments (Lane# 1-11, and 12-14).

FIG. 3: IP and immunoblot of hamster prion with various treatment. IP and immunoblot were performed under various conditions for each anti-DNA antibody. (1) Standard: IP performed in IP buffer with scrapie or normal hamster brain homogenate (lane 1, 5, 9,13,17-20). (2) DNA inhibition: 5 ug/mL phenol-chloroform extracted, ethanol precipitated, and sonicated Salmon DNA (Sigma, Mo., USA, Cat.# D7656) was added in the IP buffer as inhibitor (lane 2, 6,10, 14). (3) Proteinase K digestion: scrapie hamster brain homogenate was treated with Proteinase K at 50 ug/mL at 37 C for 1 hour. Digestion was stopped by adding Pefabic SC to a final of 4 mM. The digested homogenate was spiked in IP buffer followed by standard IP (lane 3, 7,11,15). (4) Nuclease digestion: scrapie hamster brain homogenate was treated with Benzonase® nuclease at 100 U/mL at 37 C for 1 hour. Digestion was stopped by adding EDTA to a final of 10 mM. The digested homogenate was spiked in IP buffer followed by standard IP (lane 4, 8,12,16).

Figure 4:
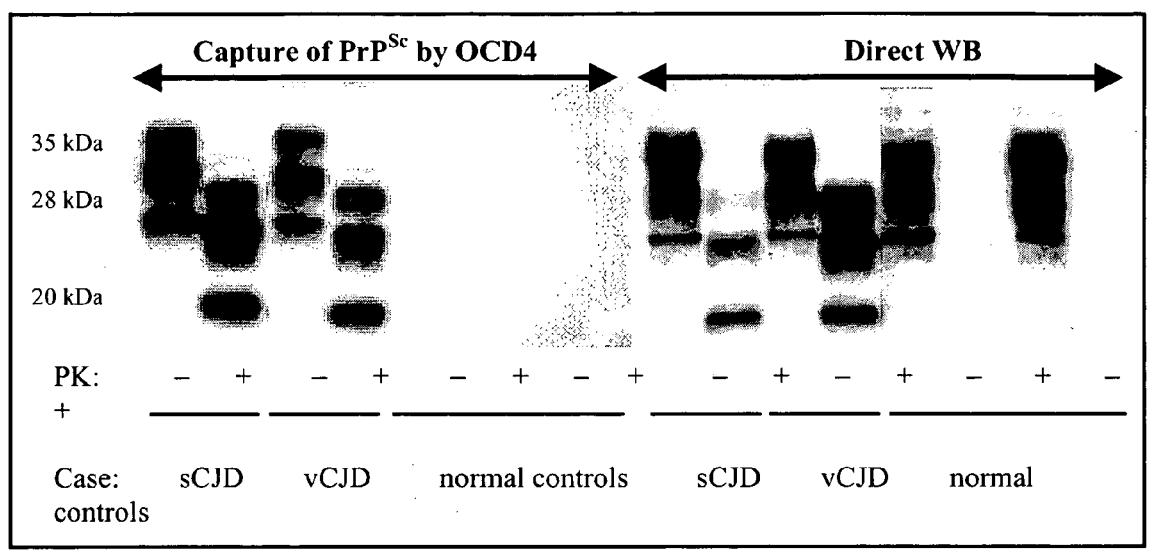

FIG. 4. Immunocapture of $PrP^{Sc}$ from brains of sCJD and vCJD by OCD4. The OCD4 conjugated beads were used to immunoprecipitate PrP in clarified brain homogenates from patients affected by either sCJD or vCJD, and two unaffected subjects (normal controls). The immunoprecipitates were then analyzed by SDS-PAGE (12% gel) and Western blotting using the anti-PrP antibody 3F4. OCD4 specifically captures $PrP^{Sc}_C$ in brains of sCJD (lane 1) and vCJD (lane 3) but not $PrP^C$ in normal brains (lanes 5 and 7). OCD4 captured PrP from sCJD and vCJD brains are authentic $PrP^{Sc}$ since treatment with PK (50 ug/ml for 1 h at 37° C.) generates the PK-resistant core $PrP^{res}$ fragments (lanes 2 and 4). Right panel. The clarified brain homogenates from sCJD, vCJD and normal controls were incubated in the absence (−) or presence (+) of PK (50 ug/ml for 1 h at 37° C.). After the PK digestion was terminated, samples were directly loaded onto SDS-PAGE gels (12%) and analyzed on Western blots using the 3F4 antibody. Brain tissues of sCJD type 2 and vCJD are well-characterized TSE reference materials from WHO.

Figure 5:
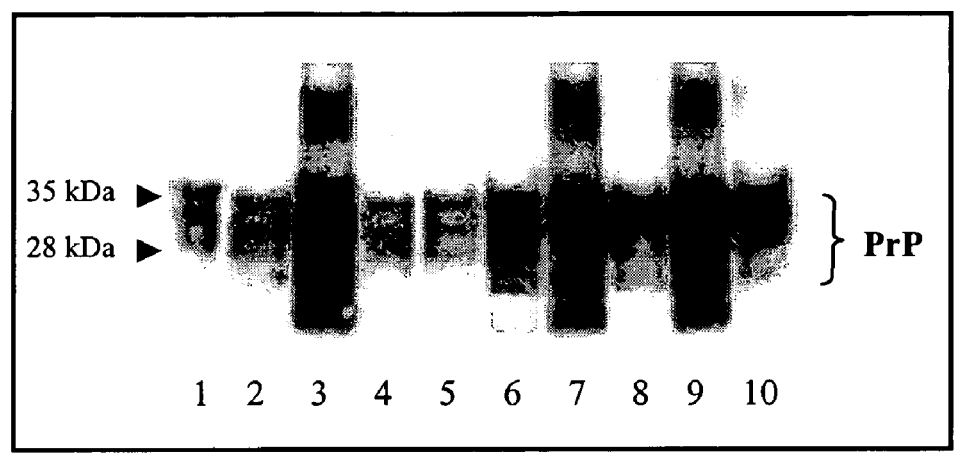

FIG. 5. The OCD4 based capture immunoassay for $PrP^{Sc}$ in brains of vCJD patients. Brain homogenates (10 ul) from 10 cases of vCJD (v1-v10) were used in the OCD4/3F4 capture immunoprecipitation assay. The experiment was conducted at the NCJDSU, UK, using kindly provided vCJD cases (case numbers: 95/052(1), 96/045(2), 97/049(3), 98/063(4), 98/148(5), 98/154(6), 99/082(7), 99/090(8), 00/066(9), 00/101(10)).

Figure 6:
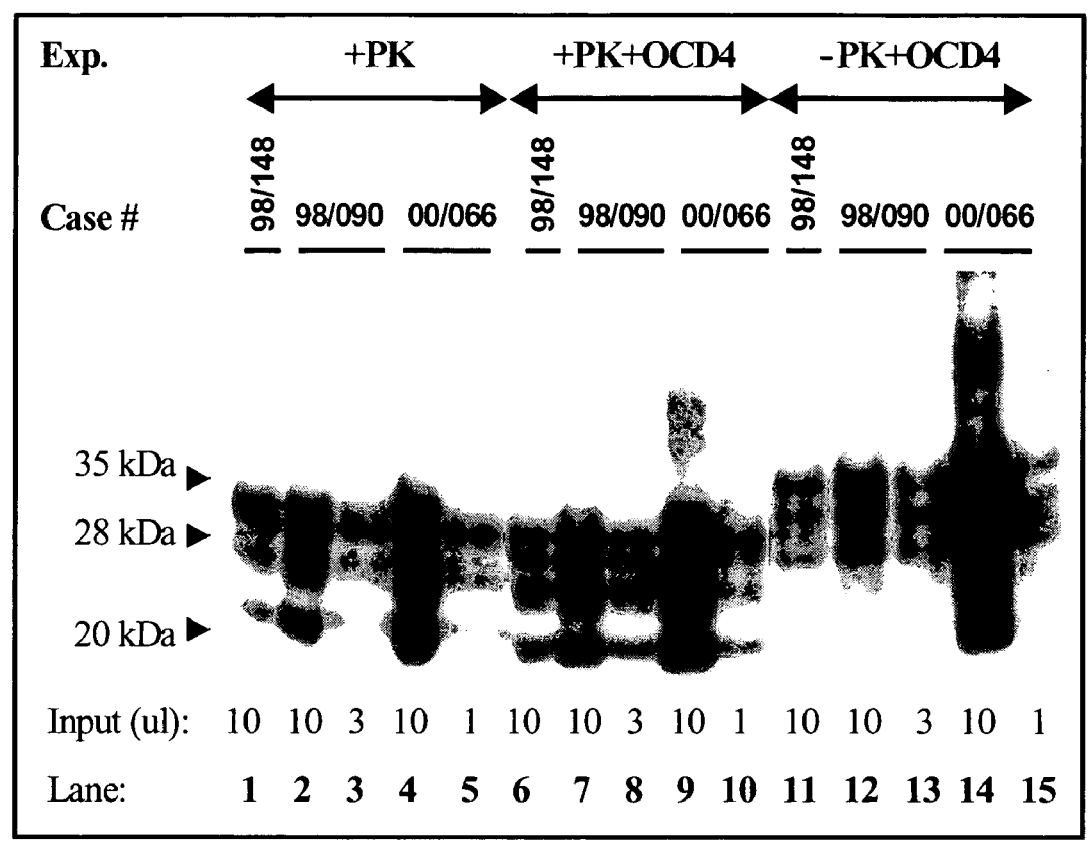

FIG. 6. Immunocapture of both the full-length $PrP^{Sc}$ and the PK-resistant core fragments by OCD4. Aliquots of brain homogenates, from three vCJD cases were used in this experiment and conducted at NCJDSU, UK. The first aliquot was digested with PK (+PK). The second aliquot was digested with PK and then was subjected to immunoprecipitation by the OCD4 (+PK+OCD4). The third aliquot underwent direct immunoprecipitation by OCD4 without the PK treatment (−PK+OCD4). All above samples were analyzed on Western blots using the 3F4 antibody. The PK-res PrP fragments (lanes 1-5) were recovered in the OCD4 immunoprecipitates (lanes 6-10). The full-length $PrP^{Sc}$ in untreated samples could be efficiently captured by OCD4 as well (lanes 11-15). Note that the input volume of the 10% brain homogenates was varied in some cases for better resolution of the PrP bands.

Figure 7:
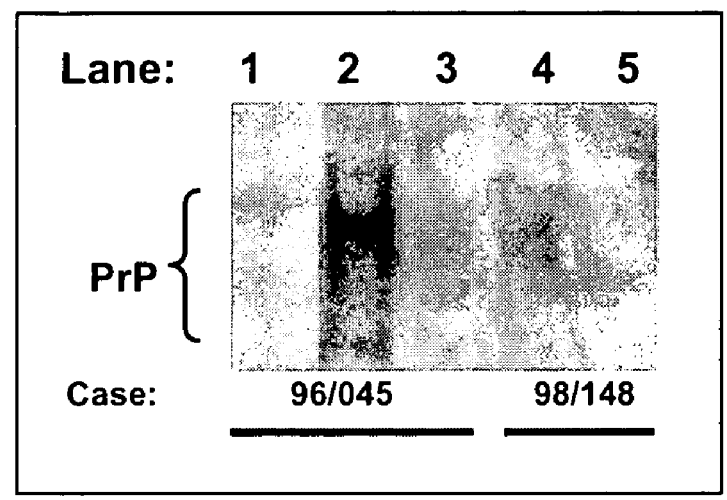

FIG. 7. OCD4 Immunocapture of PK-resistant PrP in cVJD spleen. Spleen lysate was prepared from a case of vCJD (case number 96/045 and 98/148, provided by NCJDSU at Edinburgh) using 10% homogenate followed by brief centrifuge to remove debris. PK treatment was performed at 50 ug/ml for 1 h at 37° C. before the reaction was terminated by 10 mM Pefabloc. Aliquots of each 100 ul of digested spleen lysate were either pelleted by centrifugation at 14,000 Xg for 1 h at 4° C. (lane 1), or were subjected to immunoprecipitation with OCD4 (lane 2 and 4) and with an unrelated mAb (lane 3 and 5, as control for non-specific binding). Detection of PK-resistant PrP in spleen was done on Western blots using the 3F4 antibody.

Figure 8:
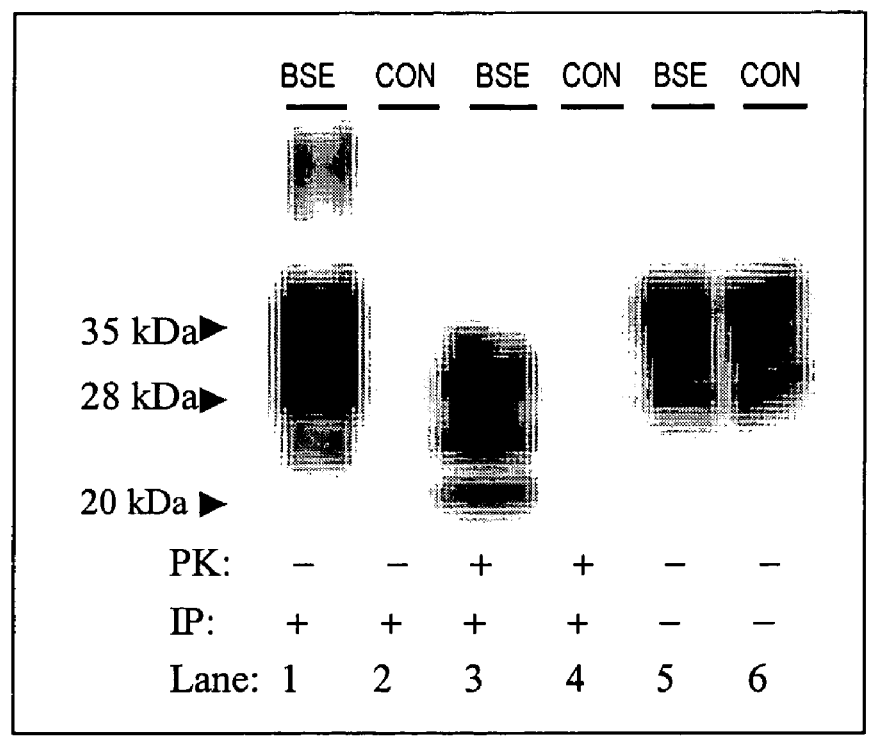

FIG. 8. OCD4 immunocapture of BSE $PrP^{Sc}$. Brain lysates (10%, w/v) from either BSE or bovine control (CON) were prepared by homogenization in lysis buffer followed by brief centrifugation. Aliquots of clarified brain lysates (1 ul each) were used in immunoprecipitation (IP) before (lanes 1 and 2) or after (lanes 3 and 4) PK digestion (50 ug/ml for 1 h at 37° C.). Additional aliquots (1 ul) without IP and PK digestion (lanes 5 and 6) served as reference for total input. All samples were then separated by SDS-PAGE and were detected on Western blots using the 6H4 antibody capable of recognizing bovine PrP. OCD4 immuoprecipitated PrP only from BSE brain in the absence or presence of PK. This experiment was conducted at the P3 facility of the Veterinary Laboratories Agency in Waybridge, London where brain tissues of BSE-affected and normal cattle were kindly provided.

Figure 9:
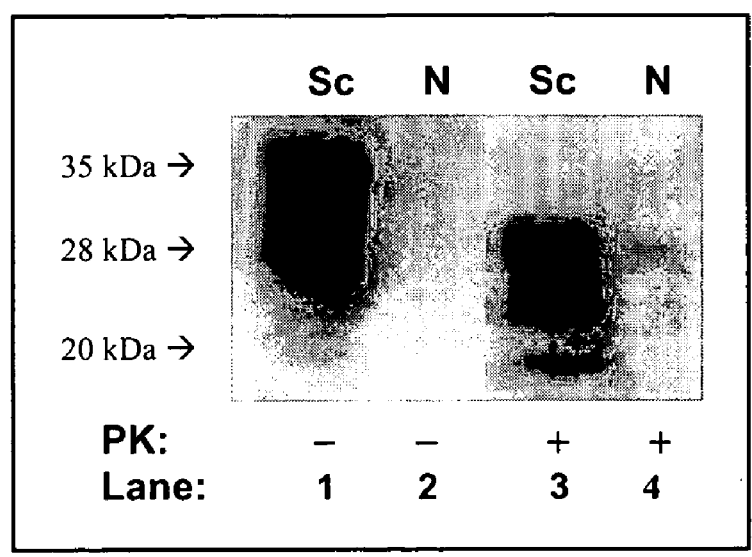

FIG. 9. OCD4 Immunocapture of $PrP^{Sc}$ in scrapie sheep. Immunoprecipitation by OCD4 of PrP from brains of natural scrapie (Sc) and normal sheep control (N) before and after treatment with PK (50 ug/ml for 1 h at 37° C.). Experiments were performed as described in the main text. Immunoprecipitates on the OCD4 conjugated beads were probed on Western blots with the 6H4 antibody on Western blots. Each assay used 1 ul of 10% brain homogenates.

Figure 10:
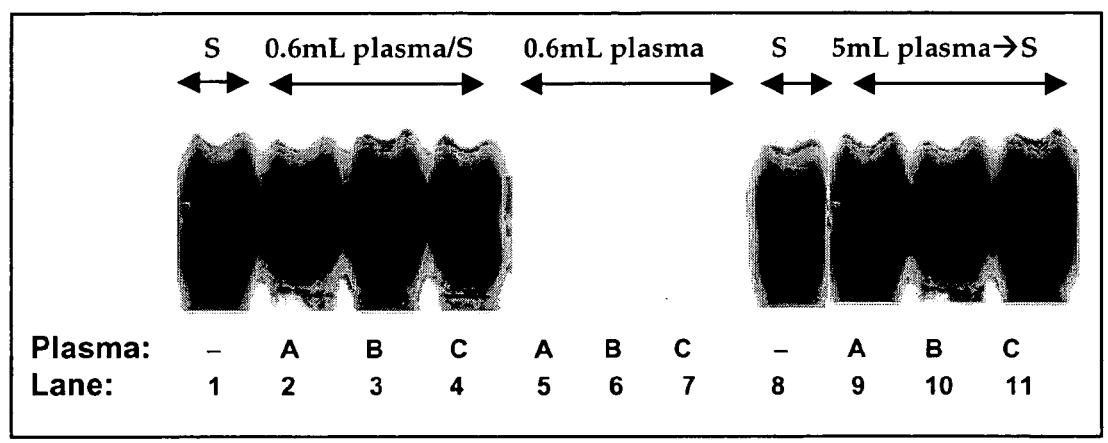

FIG. 10. Effective immunocapture of spiked $PrP^{Sc}$ in human plasma by OCD4. The spike material (S) used was 1 uL of 5% homogenate of scrapie hamster brain. Standard $PrP^{Sc}$ immunocapture in IP buffer (1 mL) was shown in lanes 1 and 8. For lanes 2-4, the spike (1 uL) was added to 0.6 ml of three normal human plasma preparations A, B, and C (0.6 ml plasma/S) with the addition of 400 uL IP buffer. Lanes 5-7 represent the non-spiked plasma aliquots (0.6 ml plasma) with 0.4 mL IP buffer. For lanes 9-11, 5 mL each of plasma A, B, and C were preincubated with the OCD4 beads followed by brief washes of the beads in PBS. The plasma treated beads were then incubated with the spike (1 uL) in 1 mL of IP buffer (5 mL plasma→S). Standard immunoprecipitation by the OCD conjugated beads was done in a total volume of 1 mL followed by Western blotting using the 3F4 antibody as described in the main text. As compared to the input control (lanes 1 and 8), significant recapture of spiked $PrP^{Sc}$ by OCD4 was achieved in plasma present in large excess (600 uL plasma vs. 1 uL spike) (lanes 2-4). Moreover, the fact that preincubation of OCD4 conjugated beads with large volume of normal plasma did not compromise or block its binding ability to capture $PrP^{Sc}$ as indicated in lane 9-11, exclude the possibility of potential OCD4 inhibitors present in human plasma. OCD4 did not capture $PrP^C$ from human plasma (lanes 5-7).

DETAILED DESCRIPTION OF THE INVENTION

The term "sample" as used herein, refers to any substance, which may contain the analyte of interest. A sample can be biological fluid, such as whole blood or whole blood components including red blood cells, white blood cells, platelets, serum and plasma, ascites, urine, cerebrospinal fluid, and other constituents of the body which may contain the analyte of interest, such as brain homogenate. Optionally, samples may be obtained from water, soil, and vegetation. The term "patient" as used herein, refers to humans and/or animals.

Various immunoassay protocols are known and could be applied to the present invention. The assay can be carried out using any enzyme label which can be attached to the anti-prion antibody to form a labelled ligand. Enzymes such as oxidases, e.g., glucose oxidase, peroxidases, e.g., horseradish peroxidase (HRP), alkaline phosphatase and galactosidases are preferred labels. It is within the skill of one of ordinary skill in the art to determine a suitable substrate for a given label. The substrate can be a material which is directly acted upon by the enzyme label or a material that is involved in a series of reactions which involve enzymatic reaction of the label. Other labels and means for detection could be for example, a ligand, nucleotide, or biotin. Detection of the labeled antibody could be by various methods including enzyme amplification with polymeric conjugates and immuno PCR.

The following examples are given to illustrate but not limit the scope of the invention.

Brain Homogenate Preparation:

Normal and scrapie hamster brain lysate were obtained from Baltimore Research and Education Foundation as 10% whole brain tissue homogenate in PBS (w/v). The lysate was further treated by adding 1/10 volume of 10X detergent homogenate buffer, composed of 5% sodium deoxycolate and 5% Igpal CA-630 (equivalent to NP-40) in PBS, incubating at 4 C for 1 hr., followed by centrifugation at 1000 g for 10 minutes. The resulting supernatant was collected and used in the assay.

Normal and BSE bovine brain tissue were provided by Veterinary Laboratories Agency (VLA), UK. Normal and scrapie sheep brain tissue were provided by Animal Disease Research Unit of USDA, USA. Normal human brain tissue were provided by National Prion Disease Pathology Surveillance Center (NPDPSC), USA. Human sCJD and vCJD brain tissue were provided by NPDPSC and National CJD Surveillance Unit (NCJDSU), UK. Brain tissue was processed the same way (or similar) as hamster brain homogenate preparation.

Anti-DNA Antibodies and DNA Binding Protein:

Monoclonal antibodies obtained from commercial sources were (1) murine monoclonal antibody recognizing ss-, ds-DNA, subclass IgM, Cat# 12403 and subclass IgG2b, Cat# 12404 from QED Bioscience, (2) murine monoclonal antibody recognizing ds-DNA, clone AE-2, subclass IgG3, Cat# 2660-2308 and murine monoclonal antibody recognizing ss-, ds-, clone 49/4A1, subclass Ig2b, Cat# 2660-2316 from Biogenesis. The immunogens used to raise these antibodies were Calf thymus DNA and nuclei from Raji Burkitts lymphoma Cells as indicated by manufactures. Additional monoclonal antibodies from other than commercial source were also evaluated. Single Stranded Binding Protein (SSB) from E.coli purchased from Sigma (Sigma, Mo., USA, Cat.# S3917).

Preparation of Immunogens:

The immunogen used to generate anti-DNA antibodies was nuclear DNA extracted from mammalian cells based upon known protocols (Sambrook 1989) and monoclonal antibodies were also generated standard protocol (Yokoyama 2001). The antibodies were screened by ELISA using the coated DNA immunogen.

Various cell lines are available to use in the identified protocols. For example, OCD4 and antibody AE-2 were generated from from DNA extracted from Raji Burkitts lymphoma cell line. One skilled in the art would certainly recognize however that other known cell lines and methods are available. For example, 49/4A1, 12403 and 12404 were generated from DNA extracted from calf thymus DNA and then screened by ELISA using the coated DNA immunogen.

OCD4 (100 μg of purified IgG) was conjugated to $7 \times 10^8$ tosyl activated superparamagnetic beads (Dynabeads M-280, Dynal Co.) in 1 ml of phosphate-buffered saline (PBS) at 37° C. for 20 h (29). The OCD4 conjugated beads were incubated with 0.1% bovine serum albumin (BSA) in (PBS) to block non-specific binding. The prepared OCD4 beads were stable for at least 3 months at 4° C. Brain homogenate (10%, w/v) was prepared in lysis buffer (100 mM NaCl, 10 mM EDTA, 0.5% Nonidet P-40, 0.5% sodium deoxycholate, 10 mM Tris-HCl, pH 7.5, and a cocktail of protease inhibitors), followed by centrifugation at 3,000×g for 10 min at 4° C. to remove debris. Immunoprecipitation was performed using 5 μl of the clarified homogenate and 10 μl of OCD4 conjugated beads in 1 ml of IP buffer containing 0.1% Tween-20 and 0.1% Nonidet P-40 in PBS, pH 7.5. After incubation with constant mixing for 2 h at room temperature, OCD4 beads were attracted to the sidewall of the plastic tubes by external magnetic force, allowing easy removal of all unbound materials in the solution. After three washes in the same buffer, OCD4 beads were collected and were boiled for 10 min in SDS sample buffer (3% sodium dodecyl sulfate (SDS), 2 mM EDTA, 10% glycerol, 50 mM Tris-HCl, pH 6.8). The eluted proteins were separated by 15% SDS-PAGE (15% Tris-glycine pre-cast gel, Bio-Rad), and were than analyzed by Western blotting either with anti-PrP antibody 3F4 recognizing residues 109-112 (17) or 6H4 recognizing residues 145-152 (14). PrP bands were visualized on Kodak X-ray film using enhanced chemiluminescence.

Conjugation of Antibody and Protein to Magnetic Beads:

0.35 mL Dynabeads® M-280 Tosylactivated (Dynal Biotech, NY, USA, Cat.# 142.03/04) were washed twice with PBS and the beads isolated from buffer with the magnet (Dynal Magnetic Particle Concentrator, MPC). 100 ug of purified antibody or protein in 1 mL PBS was added to the washed beads. Incubation with rotation was performed at 37 C for 18-20 hours. The beads were isolated from the buffer with the MPC, washed twice with 1 ml PBS (0.1% BSA), and rotated for 5 minutes at room temperature while washing. The antibody-conjugated beads were then blocked for 3-4 hours, 37° C. with 0.2 M Tris-HCl, pH 8.0, containing 0.1% BSA. The beads were subsequently washed 2 times with 1 ml PBS (0.1% BSA) and once with 1 ml PBS (0.1% BSA, 1% Tween 20) incubating each time for 10 minutes at room temp. The beads were then washed once with 1 ml PBS (0.1%BSA) and then stored in 1 ml PBS (0.05% sodium azide) at 4° C.

Proteinase K Digestion and Benzonase® Nuclease Digestion:

Conditions for the PK digestion of brain lysate: Brain homogenate was suspended in PBS buffer with or without non-ionic detergent. The total homogenate protein concentration was no more than 2.5 mg/mL. PK (Roche Diagnostics, IN, USA, Cat.# 1373196) was added to a final concentration of 50 ug/mL. Incubation was at 37 C for 0.5 to 1 hour. Digestion was stopped by adding Pefabloc SC (Roche Diagnostics, IN, USA, Cat.# 1585916) to a final concentration of 4 mM.

Conditions for the Benzonase® Nuclease digestion of brain lysate: Brain homogenate was suspended in Tris-HCl buffer, with or without non-ionic detergent, containing 2 mM $Mg^{++}$. Total homogenate protein concentration was no more than 2.5 mg/mL. Nuclease (CN Biosciences, CA, USA, Cat.# 70664) was added to a final concentration of 100 U/mL. Incubation was at 37 C for 0.5 to 1 hour. Digestion was stopped by adding EDTA to a final concentration of 10 mM.

Immunoprecipitation (IP), Non-reducing Electrophoresis and Immunoblot Detection of PrP$^{Sc}$:

Anti-DNA antibody conjugated magnetic beads were used to capture PrP$^{Sc}$ from brain homogenate by immunoprecipitation. The IP procedure consists of the following protocol: mix 100 uL antibody conjugated beads with 1-5 uL of brain homogenate in a total of 1 mL IP buffer (3% Tween20 and 3% Igpal CA-630 in PBS) and incubate at 25 C for 2.5 hours with rotation→Separate beads using MPC device and wash beads 3 times of 30 second vortexing with IP wash buffer (2% Tween20 and 2% Igpal CA-630 in PBS)→Elute captured PrP$^{Sc}$ by heating beads with NuPAGE sample buffer for 10-15 minutes. The eluted sample from IP capture were loaded onto a 4-12% NuPAGE® Bis-Tris Gel (Invitrogen, CA, USA, Cat.# NP0302) and subjected to non-reducing electrophoresis at 200V for 45 minutes. The immunoblot procedure was perfomed as follows: transfer separated proteins in the gel to a 0.2 um PVDF membrane (Invitrogen, Cat# LC2002) at 30V for 60 minutes→Block the membrane with Blocker™ Casein in TBS (0.05% Tween20) (Pierce Chemical Corp., IL, USA, Cat.# 37532) either at 25 C for 1 hour with shaking or at 4 C overnight. →As primary antibody, use 3F4 (Signet, MA, USA, Cat.# 9620-02) at 1:3000 dilution to detect hamster and human PrP$^{Sc}$ or use 6H4 (Prionics AG, Switzerland, Cat.# 01-011) at 1:5000 dilution or to detect bovine and sheep PrP$^{Sc}$ respectively. Incubate the membrane with diluted primary antibody in 10% Blocker™ Casein in TBST buffer (25 mM Tri-Cl, 0.2M NaCl, 0.2% Tween20, pH 8.0) at 25 C for 1 hour with shaking. →Wash 3× 5 minutes with TBST buffer with shaking. →Incubate membrane with horseradish peroxidase conjugated goat polyclonal anti-mouse IgG (H+L) (Jackson ImmunoResearch Laboratories, PA, USA, Cat.# 115-035-003) at 1:10,000 to 1:30,000 dilution in 50% Blocker™ Casein in TBST buffer at 25 C for 1 hour with shaking. →Wash 6× 5 minutes with TBST buffer with shaking. →Add ECL chemiluminescence substrate (Amersham Biosciences, NJ, USA, Cat.# RPN2109) or SuperSignal West Dura chemiluminescence substrate (Pierce) on membrane to develop for 5 minutes. →Take image by exposure either to Bio Max MR-2 film (Kodak, NY, USA) or to the ChemiDoc Gel Documentation System (Bio-Rad, CA, USA).

Vaccine and Therapetic Uses

Another aspect of the invention is directed toward therapeutic uses of the anti-nucleic acid antibodies as a therapeutic use. Animal models can be infected, for example with vCJD. One skilled in the art would then inject the animal with anti-nucliec acid antibodies in order to bind and neutralize the infectious prions. The result would be a reduction or elimination of the disease.

Advantages.

The present invention uses anti-DNA to capture PrP$^{Sc}$ by recognition of high affinity associated nucleic acid in the nucleic acid::PrP$^{Sc}$ complex. Because the tight association of nucleic acid only to PrP$^{Sc}$ and not to PrP$^{C}$, the present invention provided a non-intrusive means for the detection of PrP$^{Sc}$ while no PK digestion or other protein modification procedure required. It is anticipated that the mild conditions will preserve the original structure and conformation of the pathogenic prion protein, thereby offering opportunity to determine the presence of true PrP$^{Sc}$ while minimizing the generation of PrP$^{Sc}$ due to harsh sample treatment.

Provided evidence that Benzonase nuclease digestion does not compromise selective anti-DNA binding to nucleic acid::PrP$^{Sc}$, including limited endonuclease treatment in sample preparation or comprised in sample buffer could eliminate the interference of endogenous nucleic acid interference.

The use of anti-DNA antibodies offer advantages in that they display the binding specificity but can also be easily handled in direct coating to a solid phase as well as be conjugated to link to signal given reagents such as horseradish peroxidase (HRP), or to be adopted into other desired diagnosis assay format.

Literature Cited.

Alper T, Haig D, Clarke M (1966) The exceptionally small size of the scrapie agent. *Biochem. Biophys. Res. Commun.* 22:278-284

Aguzzi A, Fischer M B, (2001) Prion-Binding Activity in Serum and Plasma., US 20010053533A1

Appel T R, Dumpitak C, Matthiesen U, Riesner D. (1999) Prion rods contain an inert polysaccharide scaffold. *Biol Chem* 380(11):1295-306

Arnold, J E, Tipler C, Laszlo L, Hope J, Landon M, Mayer R J (1995) The abnormal isoform of the prion protein accumulates in late-endosome-like organelles in scrapie-infected mouse brain. *J. Pathol.* 176:403-411

Barnard G, Helmick B, Madden S, Gilbourne C and Patel R (2000) The measurement of prion protein in bovine brain tissue using differential extraction and DELFIA as a diagnostic test for BSE *Luminescence* 2000;15:357-362

Belay E D (1999) Transmissible spongiform encephalopathies in humans. *Annu. Rev. Microbiol.* 53:283-314.

Biffiger K, Zwald D, Kaufmann L, Briner A, Nayki I, Purro M, Bottcher S, Struckmeyer T, Schaller O, Meyer R, Fatzer R, Zurbriggen A, Stack M, Moser M, Oesch B, Kubler E. (2002) Validation of a luminescence immunoassay for the detection of PrP(Sc) in brain homogenate. *J Virol Methods* 101(1-2):79-84.

Bolton D C (2001) Prions and proteins: distinguishing between conformations. *The Lancet* 358(9277):164-165

Brown P, Cathala F, Raubertas R F, Gajdusek D C, Castaigne P. (1987) The epidemiology of Creutzfeldt-Jakob disease: conclusion of a 15 year investigation in France and review of the world literature. *Neurology* 37:895-904.

Brown P. The risk of bovine spongiform encephalopathy ("mad cow disease") to human health. *JAMA* 1997; 278: 1008-1011

Bruce M E, Will R G, Ironside J W, McConnell I. Drummond D, Suttie A, McCardle L, Chree A, Hope J, Birkett C, Cousens S, Fraser H and Bostock C J. (1997) Transmissions to mice indicate that 'new variant' CJD is caused by the BSE agent. *Nature* 389:498-501

Caughey B W, Dong A, Bhat K S, Ernst D, Haves S F, Caughey, W. S. (1991) Secondary structure analysis of the scrapie-associated protein PrP27-30 in water by infrared spectroscopy. *Biochemistry* 30:7672-7680.

Chandler R, (1961) Encephalopathy in mice produced with scrapie brain material. *Lancet* 1:1378-1379

Cordeiro Y, Machado F, Juliano L, Juliano M A, Brentani R R, Foguel D, Silva J L. (2001) DNA converts cellular prion protein into the beta-sheet conformation and inhibits prion peptide aggregation. *J Biol Chem.* 276(52):49400-9.

Cuillé J, Chelle P L (1936) La maladie dite tremblante du mouton est-elle inocuable? *C. R. Acad. Sci.* 203, 1552-1554

FDA and CBER, U.S. Department of Health and Human Services (2001) IV. RECOMMENDATIONS FOR DONOR DEFERRAL in Guidance for Industry: Revised Preventive Measures to Reduce the Possible Risk of Transmission of Creutzfeldt-Jakob Disease (CJD) and Variant Creutzfeldt-Jakob Disease (vCJD) by Blood and Blood Products Ferguson N M, Ghani A C, Donnelly C A, Hagenaars T J, Anderson R M. (2002) Estimating the human health risk from possible BSE infection of the British sheep flock. *Nature* 415(6870):420-4

Fischer M B, Roeckl C, Parizek P, Schwarz H P, Aguzzi A, (2000) Binding of disease-associated prion protein to plasminogen. *Nature* 408:479-83.

Foster J D, Hope J, McConnell I, Bruce M, Fraser H. (1994) Transmission of bovine spongiform encephalopathy to sheep, goats, and mice. *Ann N Y Acad Sci* 724:300-3.

Gabizon R, McKinley M P, Groth D, Prusiner S B (1988). Immunoaffinity purification and neutralization of scrapie prion infectivity. *Proc. Natl. Acad. Sci. USA* 85, 6617-6621.

Gajdusek D C, Gibbs C J J, Alpers M P (1966) Experimental transmission of a kuru-like syndrome to chimpanzees. *Nature* 209:794-796

Gajdusek D C, (1977) Unconventional viruses and the origin and disappearance of kuru. *Science* 197:943-60

Gibbs C J J, Gajdusek D C, Asher D M, Alpers M P, Beck E, Daniel P M, Matthews W B (1968) Creutzfeldt-Jakob disease (spongiform encephalopathy): transmission to the chimpanzee. *Science* 161, 388-389

Gibbs C J Jr, Gajdusek D C, Amyx H. (1979) Strain variation in the viruses of Creutzfeldt-Jakob disease and kuru. In: Prusiner S B, Hadlow W J, editors. Slow transmissible diseases of the nervous system. Volume 2. New York: Academic Press; p. 87-110.

Hill A F, Zeidler M, Ironside J, Collinge J (1997) Diagnosis of new variant Creutzfeldt-Jakob disease by tonsil biopsy. *Lancet* 349(9045):99-100

Hillier C E, Salmon R L, Neal J W, Hilton D A. (2002) Possible underascertainment of variant Creutzfeldt-Jakob disease: a systematic study. *J Neurol Neurosurg Psychiatry* 72(3):304-9

Holada K, Simak J, Vostal J G (2000) Transmission of BSE by blood transfusion.*Lancent* 356(9243):1772

Hope J, Morton L J D, Farquhar C F, Multhaup G, Beyreuther K, Kimberlin R H (1986). The major polypeptide of scrapie-associated fibrils (SAF) has the same size, charge distribution and N-terminal protein sequence as predicted for the normal brain protein (PrP). *EMBO J*. 5, 2591-2597.

Horiuchi M, Caughey B, (1999) Specific binding of normal prion protein to the scrapie form via a localized domain initiates its conversion to the protease-resistant state. *EMBO J* 18(12):3193-203.

Horwich A L, Weissman J S (1997) Deadly Conformations—Protein Misfolding in Prion Disease. *Cell*, 89:499-510

Houston F (2000) Transmission of BSE by blood transfusion in sheep. *Lancet* 356(9234):999-1000

Hunter N, Foster J, Chong A, McCutcheon S, Parnham D, Eaton S, MacKenzie C, Houston F. (2002) Transmission of prion diseases by blood transfusion. *J Gen Virol* Nov;83(Pt 11):2897-905

Jackson G S, Hosszu L L, Power A, Hill A F, Kenney J, Saibil H, Craven C J, Waltho J P, Clarke A R, Collinge J. (1999) Reversible conversion of monomeric human prion protein between native and fibrilogenic conformations. *Science* 283(5409):1935-7.

Kascsak R J, Rubenstein R, Merz P A, Tonna-DeMasi M, Fersko R, Carp R I, Wisniewski H M, Diringer H. (1987) Mouse polyclonal and monoclonal antibody to scrapie-associated fibril proteins. *J Virol*. 61(12):3688-93

Kellings K, Meyer N, Mirenda C, Prusiner S B, Riesner D. (1992). Further analysis of nucleic acids in purified scrapie prion preparations by improved return refocusing gel electrophoresis. *J. Gen. Virol*. 73, 1025-1029.

Kimberlin R H, Cole S, Walker C A. (1987) Temporary and permanent modifications to a single strain of mouse scrapie on transmission to rats and hamsters. *J Gen Virol* 68:1875-81.

Kimberlin R H, Walker C A, Fraser H. (1989) The genomic identity of different strains of mouse scrapie is expressed in hamsters and preserved on reisolation in mice. *J Gen Virol* 70:2017-25.

Klein T R, Kirsch D, Kaufmann R. and Riesner D (1998) *Biol. Chem*. 379:655-666

Korth C, Stierli B, Streit P, Moser M, Schaller O, Fischer R, Schulz-Schaeffer W, Kretzschmar H, Raeber A, Braun U, Ehrensperger F, Hornemann S, Glockshuber R, Riek R, Billeter M, Wuthrich K, Oesch B. (1997) Prion (PrPSc)-specific epitope defined by a monoclonal antibody. *Nature* 390(6655):74-7

Lasmézas C I, Deslys J P, Demaimay R, Adiou K T, Lamoury F, et al. (1996) BSE transmission to macaques. *Nature* 381:743-44

Lorenz H et al (2002) Cellular phenotyping of secretory and nuclear prion proteins associated with inherited prion diseases. *J Biol Chem Mar* 8;277(10):8508-16

Maissen M, Roeckl C, Markus G, Goldman W, Aguzzi A, (2001) Plasminogen binds to disease-associated prion protein of multiple species. *Lancet* 357:2026-8.

Manuelidis E E, Kim J H, Mericangas J R, Manuelidis L. (1985) Transmission to animals of Creutzfeldt-Jakob disease from human blood. *Lancet* 2:896-97

Marsh R F, Sipe J C, Morse S S, Hanson R P. (1976) Transmissible mink encephalopathy. Reduced spongiform degeneration in aged mink of the Chediak-Higashi genotype. *Lab Invest* 34 (4): 381-386

McBride P A, Wilson M I, eikelenboom P, Tunstall A, Bruce M E (1998) Heparan Sulfate Proteoglycan is Associated with Amyloid Plaques and Neuroanatomically Targeted PrP Pathology throughout the Incubation Period of Scrapie-Infected Mice. *Experimental Neurol*. 149:447-454

McGowan J P. (1922) Scrapie in sheep. *Scott. J. Agric*. 5:365-75

Meyer R K, McKinley M P, Bowman K A, Braunfeld M B, Barry R A, Prusiner S B (1986). Separation and properties of cellular and scrapie prion proteins. *Proc. Natl. Acad. Sci. USA* 83:2310-2314.

Moynagh J, Schimmel H, (1999) The evaluation of tests for the diagnosis of Transmissible Spongiform Encephalopathy in Bovines (8 Jul. 1999) http://europa.eu.int/comm/food/fs/bse/bse12-en.html.

Nandi P K (1998) Polymerization of human prion peptide HuPrP 106-126 to amyloid in nucleic acid solution. *Arch Virol* 143(7):1251-63.

Nandi P K, Sizaret P Y. (2001) Murine recombinant prion protein induces ordered aggregation of linear nucleic acids to condensed globular structures. *Arch. Virol*. 146(2):327-45.

Narang H K (2002) A critical review of the nature of the spongiform encephalopathy agent: prion theory versus virus theory. *Exp Biol. Med. (Maywood)* 227(1):4-19

O'Rourke K I, Baszler T V, Besser T E, Miller J M, Cutlip R C, Wells G A, et al. (2000) Preclinical diagnosis of scrapie by immunohistochemistry of third eyelid lymphoid tissue. *J Clin Microbiol* 38:3254-9.

Pan K M, Baldwin M, Nguyen J, Gasset M, Serban A, Groth D, Mehlhorn I, Huang Z, Fletterick R J, Cohen F E, Prusiner S B, (1993) Conversion of -helices into -sheets features in the formation of the scrapie prion proteins. *Proc. Natl. Acad. Sci. USA* 90:10962-10966

Parizek P, Roeckl C, Weber J, Flechsig E, Aguzzi A, Raeber A J. (2001) Similar turnover and shedding of the cellular prion protein in primary lymphoid and neuronal cells. *J Biol Chem* 276(48):44627-32

Pattison I (1957) Transmission of scrapie to the goat. *Lancet* 272:104-105.

Pattison I (1965) Resistance of the scrapie agent to formalin. *J. Comp. Pathol.* 75:159-164

Peretz D, Williamson R A, Matsunaga Y, Serban H, Pinilla C, Bastidas R B, Rozenshteyn R, James T L, Houghten R A, Cohen F E, Prusiner S B, Burton D R. (1997) A conformational transition at the N terminus of the prion protein features in formation of the scrapie isoform. *J Mol Biol* 273(3):614-22.

Prusiner S B, Novel proteinaceous infectious particles cause scrapie. *Science* (1982) 216:136-44

Riek R, Hornemann S, Wider G, Billeter M, Glockshuber R, Wuthrich K (1996). NMR structure of the mouse prion protein domain PrP(121-231). *Nature* 382:180-182

Robakis N K, Devine Gage E A, Jenkins E C, Kascsak R J, Brown W T, Krawczun M S, Silverman W P (1986) Localization of a human gene homologous to the PrP gene on the p arm of chromosome 20 and detection of PrP-related antigens in normal human brain. *Biochem. Biophys. Res. Commun.* 140, 758-765.

Saborio G P, Permanne B, Soto C, (2001) Sensitive detection of pathological prion protein by cyclic amplification of protein misfolding. *Nature* 411 (6839):810-3.

Safar J, Wille H, Itri V, Groth D, Serban H, Torchia M, Cohen F E, Prusiner S B. (1998) Eight prion strains have PrP(Sc) molecules with different conformations. *Nat. Med.* 4(10): 1157-65

Sambrook J, Fritsch E. F., Maniatis T., in *Molecular Cloning: A Laboratory Manual*, Sambrook J, Fritsch E. F., Maniatis T. Eds., Cold Spring Harbor Laboratory Press, NY, (1989), pp. 9.14-9.23

Sanghera N, Pinheiro T J (2002) Binding of prion protein to lipid membranes and implications for prion conversion. *J Mol Biol* 315(5):1241-56

Schaller O, Fatzer R, Stack M, Clark J, Cooley W, Biffiger K, Egli S, Doherr M, Vandevelde M, Heim D, Oesch B, Moser M, (1999) Validation of a western immunoblotting procedure for bovine PrP(Sc) detection and its use as a rapid surveillance method for the diagnosis of bovine spongiform encephalopathy (BSE). *Acta Neuropathol (Berl)* 98(5):437-43.

Shaked G M, Meiner Z, Avraham I, Taraboulos A, Gabizon R (2001a) Reconstitution of Prion Infectivity from Solubilized Protease-resistant PrP and Nonprotein Components of Prion Rods. *J. Biol. Chem.* 276(17):14324-14328

Shaked G M, Shaked Y, Kariv-Inbal Z, Halimi M, Avraham I, Gabizon R, (2001 b) A Protease-resistant Prion Protein Isoform Is Present in Urine of Animals and Humans Affected with Prion Diseases *J. Biol. Chem.*, 276(34):31479-82

Shyng S L, Heuser J E, Harris D A. (1994) Aglycolipid-anchored prion protein is endocytosed via clathrin-coated pits. *J. Cell Biol.* 125:1239-50

Snow A D (1990) Immunolocalization of heparan sulfate proteoglycans to the prion protein amyloid plaques of Gerstmann-Straussler syndrome, Creutzfeldt-Jakob disease and scrapie. *Lab Invest.* 63(5):601-1

Swietnicki W, Morillas M, Chen S G, Gambetti P, Surewicz W K. (2000) Aggregation and fibrillization of the recombinant human prion protein huPrP90-231. *Biochemistry* 39(2):424-31.

Taraboulos A, Serban D, Prusiner S B. (1990) Scrapie prion proteins accumulate in the cytoplasm of persistently infected cultured cells. *J. Cell. Biol.* 110:2117-32

Tateishi J. (1985) Transmission of Creutzfeldt-Jakob disease from human blood and urine into mice. *Lancet* 2:1074

Telling G C, Scott M, Mastrianni J, Gabizon R., Torchia M, Cohen F E, DeArmond S J, Prusiner S B (1995). Prion propagation in mice expressing human and chimeric PrP transgenes implicates athe interaciton of cellular PrP with another protein. *Cell* 83:79-90.

Valleron A J, Boelle P Y, Will R, Cesbron J Y. (2001) Estimation of epidemic size and incubation time based on age characteristics of vCJD in the United Kingdom. *Science* 294(5547):1726-8

Wadsworth J D, Joiner S, Hill A F, Campbell T A, Desbruslais M, Luthert P J, Collinge J. (2001) Tissue distribution of protease resistant prion protein in variant Creutzfeldt-Jakob disease using a highly sensitive immunoblotting assay. *Lancet* 358(9277):171-80

Warner R G, Hundt C, Weiss S, Turnbull J E (2002) Identification of the heparan sulfate binding sites in the cellular prion protein. *J Biol Chem.* May 24;277(21):18421-30

Weissmann C (1991) A 'unified theory' of prion propagation. *Nature* 352(6337):679-83

Wells G A H, Scott A C, Johnson C T, Gunning R F, Hancock R D, et al. (1987) A novel progressive spongiform encephalopathy in cattle. *Vet. Rec.* 31:419-20

Williams E S, Young S. (1980) Chronic wasting disease of captive mule deer: a spongiform encephalopathy. *J. Wildl. Dis.* 16:89-98

Wong B S, Brown D R, Pan T, Whiteman M, Liu T, Bu X, Li R, Gambetti P, Olesik J, Rubenstein R, Sy M S. (2001) Oxidative impairment in scrapie-infected mice is associated with brain metals perturbations and altered antioxidant activities. *J Neurochem.* 79(3):689-98.

Wong C, Xiong L W, Horiuchi M, Raymond L, Wehrly K, Chesebro B, Caughey B (2001) Sulfated glycans and elevated temperature stimulate PrPSc-dependent cell-free formation of protease-resistant prion protein *EMBO J* 20(3):377-386

Wyatt J M, Pearson G R, Smerdon T N, Gruffydd-Jones T J, Wells G A H, Wilesmith J W. (1991) Naturally occurring scrapie-like spongiform encephalopathy in five domestic cats. *Vet. Rec.* 129:233-36

Yokoyama W. M., in *Current Protocols in Cell Biology*, Bonifacino, J. S., Dasso M., Harford J. B., Lippincott-Schwartz, J., Yamada K. M., Eds. John Wiley Sons, Inc., NY (2201), pp 16.1.1-16.1.17

(RXX) Bons N, Lehmann S, Mestre-Frances N, Dormont D, Brown P, (2002) *Transfusion* May;42(5):513-6 Brain and buffy coat transmission of bovine spongiform encephalopathy to the primate *Microcebus murinus.*

We claim:

1. An immunoassay for detecting infectious prions comprising:

providing a solid support having bound thereto an anti-nucleic acid antibody, wherein the anti-nucleic acid antibody binds to deoxyribonucleic acid present in infectious prions found in Creutzfeldt-Jakob Disease brain homogenates, contacting the solid support with a sample, wherein deoxyribonucleic acid which is present in infectious prions that are present in the sample binds to the anti-nucleic acid antibody thereby capturing any infectious prions on the solid support, washing the support to remove any unbound sample, contacting the solid support with a labeled prion specific antibody, wherein the labeled prion specific antibody binds to any captured infectious prions, and carrying out a detection step to determine if infectious prions are bound to the solid support.

2. An immunoassay for detecting infectious prions comprising:

providing a solid support coated with an agent to bind an anti-nucleic acid antibody, contacting the solid support with an anti-nucleic acid antibody, wherein the anti-nucleic acid antibody binds to deoxyribonucleic acid present in infectious prions found in Creutzfeldt-Jakob Disease brain homogenates, wherein the anti-nucleic ac